United States Patent [19]

Koga et al.

[11] Patent Number: 5,336,766
[45] Date of Patent: Aug. 9, 1994

[54] INDOLEACETIC ACID SYNTHETASE-ENCODING GENE

[75] Inventors: Jinichiro Koga; Takashi Adachi; Hidemasa Hidaka, all of Saitama, Japan

[73] Assignee: Meiji Seika Kaisha, Ltd., Tokyo, Japan

[21] Appl. No.: 662,223

[22] Filed: Feb. 28, 1991

[30] Foreign Application Priority Data

Feb. 28, 1990 [JP] Japan .................. 2-45718

[51] Int. Cl.$^5$ .................. C12N 15/60; C12N 9/88; C12N 15/00; C12P 19/34
[52] U.S. Cl. .................. 536/23.2; 435/69.1; 435/71.2; 435/172.3; 435/232; 435/252.3; 435/320.1; 935/14; 935/29; 935/56
[58] Field of Search .................. 435/69.1, 71.2, 172.3, 435/232, 252.3, 320.1; 935/9, 11, 14, 23, 29, 56; 536/27

[56] References Cited

PUBLICATIONS

Physiological Plant Pathology, 13, pp. 203–214, 1978.
Eur. J. Biochem. 138, pp. 387–391, 1984.
Biol. Rev. 48, pp. 510–515, 1973.
Proc. Natl. Acad. Sci. USA, 81, pp. 1728–1732, 1984.
Proc. Natl. Acad. Sci USA, 82, pp. 6522–6526, 1985.
Koga et al., Mol. Gen. Genet., 226, 10–16 (1991).
Koga et al., Agric Biol. Chem. 55(3), 701–706 (1991).
European Search Report.
Patent Abstracts of Japan, vol. 12, No. 258 (C–513)(3105), Jul. 20, 1988; & JP-A-63042693 (NOK Corp.) Feb. 23, 1988.
Proceedings of the National Academy of Sciences of the United States of America, vol. 82, No. 19, Oct. 1985, pp. 6522–6526, Wash., D.C., US; T. Yamada et al.: "Nucleotide sequences of the Pseudomonas savastanoi indoleacetic acid genes show homology with Agrobacterium tumefaciens T-DNA".
Patent Abstracts of Japan, vol. 12, No. 496 (C–555)(3343), Dec. 23, 1988; & JP-A-63207379 (NOK Corp.) May 1, 1989.
Patent Abstracts of Japan, vol. 13, No. 336 (C–623)(3684), Jul. 27, 1989; & JP-A-01112994 (NOK Corp.) May 1, 1989.
Proceedings of the National Academy of Sciences of the United States of America, vol. 81, No. 6, Mar. 1984, pp. 1728–1732, Wash., D.C, US; H. Klee et al.: "Nucleotide sequence of the tms genes of the pTiA6NC octopine Ti plasmid: Two gene products involved in plant tumorigenesis".

*Primary Examiner*—Robert A. Wax
*Assistant Examiner*—Rebecca Prouty
*Attorney, Agent, or Firm*—Sughrue, Mion, Zinn, Macpeak & Seas

[57] ABSTRACT

An *Enterobacter cloacae*-derived gene encoding an enzyme involved in the biosynthetic pathway from tryptophan to indoleacetic acid via indolepyruvic acid and indoleacetaldehyde as intermediates.

3 Claims, 3 Drawing Sheets

```
  1  ATG CGA ACC CCA TAC TGC GTC GCC GAT TAC CTG CTG GAC CGT CTT ACA GAT TGT GGT GCC   60
  1   M   R   T   P   Y   C   V   A   D   Y   L   L   D   R   L   T   D   C   G   A    20

61  GAT CAT CTG TTT GGC GTG CCG GGC GAC TAT AAC CTG CAG TTT CTC GAC CAC GTA ATA GAC  120
 21   D   H   L   F   G   V   P   G   D   Y   N   L   Q   F   L   D   H   V   I   D    40

121  AGC CCG GAT ATT TGT TGG GTG GGC TGT GCC AAT GAG CTG AAC GCA GCA TCC TAT GCT GAC  180
 41   S   P   D   I   C   W   V   G   C   A   N   E   L   N   A   A   S   Y   A   D    60

181  GGA TAC GCC CGA TGT CGA GGC AAG GGC TTT GCC GCG CTA CTG ACC ACA TTC GGC GTT TTA  240
 61   G   Y   A   R   C   R   G   K   G   F   A   A   L   L   T   T   F   G   V   L    80

241  AGT GCC ATG AAC GCC ATT GCC TAT GCC AGC TAT GAG CAT GTC ACA TTC GGG GAG ATT GTG  300
 81   S   A   M   N   A   I   A   Y   A   S   Y   E   H   V   T   F   G   E   I   V    100

301  GGG GCG CCG GGT ACG GGT CAA CAG CAA CGG GGA GAG GAG CAT CTG CTG CAT CAT TTG GGG  360
101   G   A   P   G   T   G   Q   Q   Q   R   G   E   E   H   L   L   H   H   L   G    120

361  GGG GAG TTC CGT CAC TTT TAT CAT GAG ATG AGC GAG CCG ATC GTC GCA CAG ACG CTT GGG  420
121   G   E   F   R   H   F   Y   H   E   M   S   E   P   I   V   A   Q   T   L   G    140

421  ACC GAA CAA AAT GCC TGT TAT GAA ATC GAC CGT GTG TTG ACA ACC ATG CGT GAA CGC  480
141   T   E   Q   N   A   C   Y   E   I   D   R   V   L   T   T   M   R   E   R    160

481  CGC CCC TAT CTG ATG TTA CCC GGC GAT GTG GCA AAA AAA GCC GCC ACG CCG CCT GTA  540
161   R   P   Y   L   M   L   P   G   D   V   A   K   K   A   A   T   P   P   V    180

541  AAC GCT CTC ACT CAT AAG CAG GCT CAT GCC GAT AGC GCC CTG AAA TGC CTG AAA GCG TTC CGG GAT  600
181   N   A   L   T   H   K   Q   A   H   A   D   S   A   L   K   C   L   K   A   F   R   D  200
```

```
601  GCT GCT GAG AAC AAA CTG GCG ATG AGC AAA CGT ACC GCC CTG CTG GCC GAC TTC CTT GTT   660
201   A   A   E   N   K   L   A   M   S   K   R   T   A   L   L   A   D   F   L   V   220

661  CTG CGC CAT GGC CAT GGC CTG ATG AGC CTA AAA CAT CAG AAG AGG TGG GTA GAG CCG ATG   720
221   L   R   H   G   H   G   L   M   S   L   K   H   Q   K   R   W   V   E   P   M   240

721  GCC ACC ATG CTG ATG CTG ATG GGG AAA ATA TTC GAC GAG CGT CAG GGT TTT TAC GGC ACA   780
241   A   T   M   L   M   L   M   G   K   I   F   D   E   R   Q   G   F   Y   G   T   260

781  TAC AGT GGT TCA GCC AGC ACT GGC GCG GTA AAA GAG GCG CAG GCT GAC CAC CAG GGC GTA   840
261   Y   S   G   S   A   S   T   G   A   V   K   E   A   Q   A   D   H   Q   G   V   280

841  TTG TGT GTT GGC ACG TTT ACC GAT CCG ATT GAA GGG GCT CAC CAG TGG CTT ACG ACC ACC   900
281   L   C   V   G   T   F   T   D   P   I   E   G   A   H   Q   W   L   T   T   T   300

901  CCG GCG CAG CGT ACC ACC CAT CCG GCC CTG ACG TTC GGG GCT CAC CAG CGT CTC GAC GTG CAT   960
301   P   A   Q   R   T   T   H   P   A   L   T   F   G   A   H   Q   R   L   D   V   H   320

961  GGC ATC CCA ATG AAC ATT GCC GCG ACG GTC GGG GAC CAC GGT TCG CTT TTT ACC   1020
321   G   I   P   M   N   I   A   A   T   V   G   D   H   G   S   L   F   T   340

1021 GCT GGC CTT ATG TCA TCC GGC ACG ATA CCG TTC GCG GAC CCG GAC ATT ATC ATC CTT   1080
341   A   G   L   M   S   S   G   T   I   P   F   A   D   P   D   I   I   L   360

1081 ACC CAG GAG AAT TTC TGG AGA ACG TTG CAA ACC TTT CTG TTA CCG GGG GAC GTG TCG CTT   1140
361   T   Q   E   N   F   W   R   T   L   Q   T   F   L   L   P   G   D   V   S   L   380

1141 GCC GAC CAG CAG GGA ACA TCG GGC TTC GGC GCG ATT GAT CTG CGT CCG GCT GTG AAC   1200
381   A   D   Q   Q   G   T   S   G   F   G   A   I   D   L   R   P   A   V   N   400
```

```
1201  TTT ATC GTC CAG CCG CTG TGG GGC TCG ATT GGT TAC ACG CTG GCG GCG TTT GGT GCA  1260
 401   F   I   V   Q   P   L   W   G   S   I   G   Y   T   L   A   A   F   G   A   420

1261  CAA ACC GCA TGC CCG AAC CGG CGC GTG ATT GTG CTG ACG ACG GAT GCT GCC CAG CTC  1320
 421   Q   T   A   C   P   N   R   R   V   I   V   L   T   T   D   A   A   Q   L   440

1321  ACT ATT CAG GAA CTA GGT TAC TAC GGT CTG CGT GAT AAA CTG CTG GGG GAT CCC GCT GCC CAG  1380
 441   T   I   Q   E   L   G   Y   Y   G   L   R   D   K   L   L   G   D   P   A   Q   460

1381  AAC AAC GAA GGT CTA AAC AGG ATG CGT GTT TCG CGA GCC TGG GAG CAG CAC CCC GAT CAG AAC  1440
 461   N   N   E   G   L   N   R   M   R   V   S   R   A   W   E   Q   H   P   D   Q   N

1441  ATT GCT TTG TGG AAC TAC AGT ATT CAG CAC ATT GCG CGG GCG ATC CTC GAG CAG TCT  1500
 481   I   A   L   W   N   Y   S   I   Q   H   I   A   R   A   I   L   E   Q   S   500

1501  TGC TGG CGG GTC AGT TGG ACG GCG CAG GCG TTG CTT GAA CAG GAC GTA CTT GAG CAC  1560
 501   C   W   R   V   S   W   T   A   Q   A   L   L   E   Q   D   V   L   E   H   520

1561  GAG CGG CTC TCG TCG TTG ATT GAG GTG ATG CTC CCG AAA GCC GAT ATC CCG CTG CTC  1620
 521   E   R   L   S   S   L   I   E   V   M   L   P   K   A   D   I   P   L   L   540

1621  GCG CTT ACC AAG GCT CTG GAA GCG TGT AAT AAC GCC TGA                          1659
 541   A   L   T   K   A   L   E   A   C   N   N   A   *
```

FIG. 1C

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1659 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( v i ) ORIGINAL SOURCE:
        ( A ) ORGANISM: Enterobacter cloacae ( v i i ) IMMEDIATE SOURCE:
        ( A ) LIBRARY: genomic
        ( B ) CLONE: PIA119

( i x ) FEATURE:
        ( A ) NAME/KEY: matpeptide
        ( B ) LOCATION: 1..1659
        ( D ) OTHER INFORMATION:
            / product="indoleacetic acid synthetase"

( x i ) SEQUENCE DESCRIPTION: SEQ ID NO:1:

```
ATGCGAACCC CATACTGCGT CGCCGATTAC CTGCTGGACC GTCTTACAGA TTGTGGTGCC      60
GATCATCTGT TTGGCGTGCC GGGCGACTAT AACCTGCAGT TTCTCGACCA CGTAATAGAC     120
AGCCCGGATA TTTGTTGGGT GGGCTGTGCC AATGAGCTGA ACGCATCCTA TGCCGCTGAC     180
GGATACGCCC GATGTAAGGG CTTTGCCGCG CTACTGACCA CATTCGGCGT TGGGGAGTTA     240
AGTGCCATGA ACGGCATTGC CGGCAGCTAT GCCGAGCATG TCCCGGTTTT ACATATTGTG     300
GGGGCGCCGG GTACGGCGGC ACAGCAAAGG GGAGAGTTGC TGCATCATAC GTTGGGGGAT     360
GGGGAGTTCC GTCACTTTTA TCATATGAGC GAGCCGATCA CCGTCGCACA GGCGGTCCTT     420
ACCGAACAAA ATGCCTGTTA TGAAATCGAC CGTGTGTTGA CAACCATGCT TCGGGAACGC     480
CGCCCCGGTT ATCTGATGTT ACCCGCCGAT GTGGCAAAAA AAGCCGCCAC GCCGCCTGTA     540
AACGCTCTCA CTCATAAGCA GGCTCATGCC GATAGCGCCT GCCTGAAAGC GTTCCGGGAT     600
GCTGCTGAGA ACAAACTGGC GATGAGCAAA CGTACCGCGC TGCTGGCCGA CTTCCTTGTT     660
```

-continued

```
CTGCGCCATG GCCTGAAACA TGCGCTACAG AAGTGGGTGA AAGAGGTACC GATGGCCCAT      720
GCCACCATGC TGATGGGGAA AGGGATATTC GACGAGCGTC AGGCGGGTTT TTACGGCACA      780
TACAGTGGTT CAGCCAGCAC TGGCGCGGTA AAAGAGGCGA TTGAAGGGGC TGACACGGTA      840
TTGTGTGTTG GCACGCGTTT TACCGATACC CTGACGGCCG GGTTCACGCA CCAGCTTACC      900
CCGGCGCAGA CCATTGAAGT TCAGCCGCAT GCCGCACGCG TCGGGGATGT CTGGTTTACC      960
GGCATCCCAA TGAACCAGGC GATTGAGACG CTGGTCGAAC TCTGCAAACA GCACGTGCAT     1020
GCTGGCCTTA TGTCGTCATC ATCCGGCGCA ATACCGTTCC CGCAGCCGGA CGGTTCGCTT     1080
ACCCAGGAGA ATTTCTGGAG AACGTTGCAA ACCTTTATTC GCCCGGGGA CATTATCCTT      1140
GCCGACCAGG AACATCGGC CTTCGGCGCG ATTGATCTGC GTTACCGGC TGATGTGAAC       1200
TTTATCGTCC AGCCGCTGTG GGGCTCGATT GGTTACACGC TGGCGGCGGC GTTTGGTGCA     1260
CAAACCGCAT GCCCGAACCG GCGCGTGATT GTGCTGACGG GGATGGCGC TGCCCAGCTC      1320
ACTATTCAGG AACTAGGCTC GATGCTGCGT GATAAACAGC ACCCCATTAT TCTGGTGCTC     1380
AACAACGAAG GTTACACGGT TGAGAGGGCT ATCCACGGGG CGGAGCAGCG GTATAACGAC     1440
ATTGCTTTGT GGAACTGGAC GCACATTCCG CAGGCGTTGA GCCTCGATCC TCAGTCTGAG     1500
TGCTGGCGGG TCAGTGAAGC GGAACAGCTG GCGGACGTAC TTGAAAAAGT GGCGCACCAC     1560
GAGCGGCTCT CGTTGATTGA GGTGATGCTC CCGAAAGCGG ATATCCCGCC GCTGCTCGGG     1620
GCGCTTACCA AGGCTCTGGA AGCGTGTAAT AACGCCTGA                            1659
```

( 2 ) INFORMATION FOR SEQ ID NO:2:

( i ) SEQUENCE CHARACTERISTICS:
    ( A ) LENGTH: 552 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: Y ( v i ) ORIGINAL SOURCE:
    ( A ) ORGANISM: Enterobacter cloacae ( i x ) FEATURE:
    ( A ) NAME/KEY: Protein
    ( B ) LOCATION: 1..552
    ( D ) OTHER INFORMATION:
      / note="indoleacetic acid synthetase"

( x i ) SEQUENCE DESCRIPTION: SEQ ID NO:2:

```
Met Arg Thr Pro Tyr Cys Val Ala Asp Tyr Leu Leu Asp Arg Leu Thr
 1               5                  10                  15

Asp Cys Gly Ala Asp His Leu Phe Gly Val Pro Gly Asp Tyr Asn Leu
            20                  25                  30

Gln Phe Leu Asp His Val Ile Asp Ser Pro Asp Ile Cys Trp Val Gly
        35                  40                  45

Cys Ala Asn Glu Leu Asn Ala Ser Tyr Ala Ala Asp Gly Tyr Ala Arg
    50                  55                  60

Cys Lys Gly Phe Ala Ala Leu Leu Thr Thr Phe Gly Val Gly Glu Leu
65                  70                  75                  80

Ser Ala Met Asn Gly Ile Ala Gly Ser Tyr Ala Glu His Val Pro Val
                85                  90                  95

Leu His Ile Val Gly Ala Pro Gly Thr Ala Ala Gln Gln Arg Gly Glu
            100                 105                 110

Leu Leu His His Thr Leu Gly Asp Gly Glu Phe Arg His Phe Tyr His
        115                 120                 125
```

```
Met Ser Glu Pro Ile Thr Val Ala Gln Ala Val Leu Thr Glu Gln Asn
    130             135             140
Ala Cys Tyr Glu Ile Asp Arg Val Leu Thr Thr Met Leu Arg Glu Arg
145             150             155             160
Arg Pro Gly Tyr Leu Met Leu Pro Ala Asp Val Ala Lys Lys Ala Ala
                165             170             175
Thr Pro Pro Val Asn Ala Leu Thr His Lys Gln Ala His Ala Asp Ser
            180             185             190
Ala Cys Leu Lys Ala Phe Arg Asp Ala Ala Glu Asn Lys Leu Ala Met
        195             200             205
Ser Lys Arg Thr Ala Leu Leu Ala Asp Phe Leu Val Leu Arg His Gly
    210             215             220
Leu Lys His Ala Leu Gln Lys Trp Val Lys Glu Val Pro Met Ala His
225             230             235             240
Ala Thr Met Leu Met Gly Lys Gly Ile Phe Asp Glu Arg Gln Ala Gly
                245             250             255
Phe Tyr Gly Thr Tyr Ser Gly Ser Ala Ser Thr Gly Ala Val Lys Glu
            260             265             270
Ala Ile Glu Gly Ala Asp Thr Val Leu Cys Val Gly Thr Arg Phe Thr
        275             280             285
Asp Thr Leu Thr Ala Gly Phe Thr His Gln Leu Thr Pro Ala Gln Thr
    290             295             300
Ile Glu Val Gln Pro His Ala Ala Arg Val Gly Asp Val Trp Phe Thr
305             310             315             320
Gly Ile Pro Met Asn Gln Ala Ile Glu Thr Leu Val Glu Leu Cys Lys
                325             330             335
Gln His Val His Ala Gly Leu Met Ser Ser Ser Gly Ala Ile Pro
            340             345             350
Phe Pro Gln Pro Asp Gly Ser Leu Thr Gln Glu Asn Phe Trp Arg Thr
        355             360             365
Leu Gln Thr Phe Ile Arg Pro Gly Asp Ile Ile Leu Ala Asp Gln Gly
    370             375             380
Thr Ser Ala Phe Gly Ala Ile Asp Leu Arg Leu Pro Ala Asp Val Asn
385             390             395             400
Phe Ile Val Gln Pro Leu Trp Gly Ser Ile Gly Tyr Thr Leu Ala Ala
                405             410             415
Ala Phe Gly Ala Gln Thr Ala Cys Pro Asn Arg Arg Val Ile Val Leu
            420             425             430
Thr Gly Asp Gly Ala Ala Gln Leu Thr Ile Gln Glu Leu Gly Ser Met
        435             440             445
Leu Arg Asp Lys Gln His Pro Ile Ile Leu Val Leu Asn Asn Glu Gly
    450             455             460
Tyr Thr Val Glu Arg Ala Ile His Gly Ala Glu Gln Arg Tyr Asn Asp
465             470             475             480
Ile Ala Leu Trp Asn Trp Thr His Ile Pro Gln Ala Leu Ser Leu Asp
                485             490             495
Pro Gln Ser Glu Cys Trp Arg Val Ser Glu Ala Glu Gln Leu Ala Asp
            500             505             510
Val Leu Glu Lys Val Ala His His Glu Arg Leu Ser Leu Ile Glu Val
        515             520             525
Met Leu Pro Lys Ala Asp Ile Pro Pro Leu Leu Gly Ala Leu Thr Lys
    530             535             540
Ala Leu Glu Ala Cys Asn Asn Ala
545             550
```

INDOLEACETIC ACID SYNTHETASE-ENCODING GENE

FIELD OF THE INVENTION

This invention relates to a gene encoding an enzyme involved in the biosynthetic pathway from tryptophan to indoleacetic acid via indolepyruvic acid and indoleacetaldehyde as intermediates.

BACKGROUND OF THE INVENTION

Indoleacetic acid (IAA) is a typical plant hormone. Its actions that have been demonstrated include, among others, promoting plant rooting, inducing stem and leaf elongation, inducing parthenocarpy and preventing aging. IAA is therefore a substance of considerable significance from the plant physiology viewpoint. It has been established that IAA is produced not only by plants but also by microorganisms and animals. As regards microorganisms, in particular, various investigations are in progress concerning the meaning of the production of plant hormones by bacteria occurring on or in the plant stem, leaf and root regions. Thus, for instance, it has been shown that *Pseudomonas syringae* pv. savastanoi infects olives and produces IAA, leading to tumor formation (Physiol. Plant Pathol., 13, 203–214, 1978). Furthermore, *Agrobacterium tumefaciens* infects dicotyledons and the T-DNA region of the Ti plasmid carried by this microorganism is integrated into the nucleus of said plants causing formation of tumors called crown galls. It has been revealed that the T-DNA contains a gene involved in the biosynthesis of IAA (Eur. J. Biochem., 138, 387–391, 1984).

It has been established that IAA is generally produced from tryptophan as a precursor via the following three biosynthetic pathways (Biol. Rev., 48, 510–515, 1973).

1) Tryptophan→indoleacetamide→IAA;
2) Tryptophan→tryptamine→indoleacetaldehyde→IAA;
3) Tryptophan→indolepyruvic acid→indoleacetaldehyde→IAA.

The Pseudomonas and Agrobacterium species mentioned above have been shown to produce IAA by the biosynthetic pathway 1), and the enzymes involved therein and the genes coding therefor have been isolated (Proc. Natl. Acid. Sci. USA, 81, 1728–1732, 1984; ibid., 82, 6522–6526, 1985).

On the other hand, as regards the biosynthetic pathway 3), which is considered to be the main one in plants, neither the enzymes involved therein nor the genes coding therefor have been isolated because of instability of the intermediates involved. Accordingly, the mechanisms of control thereof have not been made clear as yet. As the above facts suggest, the plant physiology of IAA, a representative plant hormone, remains unknown in many respects and its functions have been known only insufficiently.

SUMMARY OF THE INVENTION

An object of the present invention is to isolate a gene encoding the biosynthetic route to IAA, to reveal the structure thereof, to introduce IAA gene of an enzyme or enzymes involved in the biosynthetic route to IAA into a plant or microorganism, to create a novel plant or microorganism of industrial value, and to utilize the same commercially.

As a result of intensive investigation, the present inventors found that *Enterobacter cloacae* isolated from the root region of a plant has the ability to produce IAA as one of the mechanisms of its plant growth promoting action. They also found, by identifying the reactions involved in conversion to IAA from its precursor, that the biosynthetic pathway to IAA involves indolepyruvic acid and indoleacetaldehyde as intermediates in the same manner as in plants. Furthermore, they isolated a DNA corresponding to the full-length IAA synthetase gene, introduced said DNA into *Escherichia coli*, confirmed the function of said gene by verifying the ability of an *Escherichia coil* transformant obtained by introducing said gene thereinto to produce IAA and determined the base sequence of said gene.

Thus the gist of the invention consists of a gene borne by *Enterobacter cloacae* and involved in the biosynthesis of IAA from tryptophan via indolepyruvic acid and indoleacetaldehyde as intermediates.

BRIEF DESCRIPTION OF THE DRAWINGS

FIGS. 1A–1C show a gene encoding indoleacetic acid synthetase. Amino acids are indicated according to the "one-letter notation" ["Seikagaku Jiten (Dictionary of Biochemistry)". published by Tokyo Kagaku Dojin, page 1392, 1984].

DETAILED DESCRIPTION OF THE INVENTION

*Enterobacter cloacae* isolated from the root region of a plant has been deposited with the Fermentation Research Institute, Agency of Industrial Science and Technology of Japan, of 1–3, Higashi 1-chome, Tsukuba-shi, Ibaraki 305 Japan, since Sep. 12, 1986 under the deposit number FERM BP-1529 in accordance with the Budapest Treaty.

The IAA synthetase gene according to the present invention is isolated in the following manner.

*Enterobacter cloacae* is suspension-cultured in LB medium (1% Bactotryptone (Difco), 0.5% yeast extract (Difco) and 0.5% NaCl, pH 7.0) at 37° C. for 24 hours with shaking. The nuclear DNA is extracted from the cells obtained by the alkaline method. This nuclear DNA is partially digested with Sau3AI and the resulting fragments are inserted into the plasmid pUC119 (Takara Shuzo) at the BamHI site. Usable plasmids are pUC118 (Takara Shuzo), PTZ19 and PTZ18 (Toyobo). The resulting recombinant plasmid DNA mixture is used to transform host cells such as *Escherichia coli* DH5α, JM109, JM105, DH1 and HB101 to give a genomic library. Preferred as a host is *E. coli* DH5α (BRL) which is incapable of producing IAA. Colonies are each suspension-cultured in LB medium at 37° C. for 24 hours. A clone having the IAA biosynthesis gene can be obtained by selecting an IAA producer. The base sequence of the thus-obtained IAA biosynthesis gene is determined by the dideoxy method and the corresponding amino acid sequence is as shown in FIGS. 1A–1C.

The following examples are further illustrative of the present invention but are by no means limitative of the scope thereof.

The techniques, reactions and analysis for use in the practice of the invention are well known in the art, as described in Molecular Cloning, a laboratory mannual, Cold Spring Harbor Laboratory Press, New York.

EXAMPLE 1

Nuclear DNA isolation from *Enterobacter cloacae* by the alkaline method

*Enterobacter cloacae* (FERM BP-1529) was shake-cultured in 100 ml of LB medium at 37° C. for 24 hours. Cells were recovered by centrifuging the culture at 10,000 revolutions per minute for 20 minutes. The cells were suspended in 16 ml of a TESH solution (0.2M Tris-HCl, 0.02M EDTA, 0.05M NaCl, pH 8.0). To the suspension were added 4 ml of 0.5M EDTA, 0.2 ml of 0.5% RNase A (Sigma) and 0.2 ml of egg white lysozyme (Sigma). The mixture was incubated at 37° C. for 2 hours. Then 1 ml of 5% SDS solution was added and the resultant mixture was incubated overnight at 37° C. with gentle stirring. To this reaction mixture was added an equal volume of phenol-saturated TESH solution. The mixture was shaken at room temperature for 10 minutes and then centrifuged at 3,500 revolutions per minute at room temperature for 10 minutes. The aqueous layer was taken up with care to exclude the intermediate layer and subjected to three repetitions of the above-mentioned phenol treatment. Two volumes of ethanol were added to the aqueous layer thus obtained and the nuclear DNA was rolled around a glass rod with stirring therewith and resolved in a TE solution (0.01M Tris-HCl, 0.001M EDTA, pH 8.0) to give a nuclear DNA solution.

EXAMPLE 2

Preparation of an Enterobacter cloacae-derived genomic library (1) Sau3AI (Toyobo) was added, in amounts of 0.25, 0.5, 1, 2, 4, 8 and 16 units, to respective 100-μl portions of the nuclear DNA solution (450 μg/ml) prepared from *Enterobacter cloacae* as described in Example 1 and each mixture was incubated at 37° C. for 30 minutes. The reaction mixtures were examined by agarose gel electrophoresis. Those reaction mixtures that contained DNAs of 1 to 20 kbp in length were pooled and subjected to three repetitions of phenol extraction (phenol-chloroform-isoamyl alcohol=50:49:1 by volume). To the solution thus obtained was added 1/10 volume of 3 N sodium acetate and 2 volumes of ethanol, and the mixture was cooled at −20° C. for 20 minutes and then centrifuged. The DNA thus recovered was washed with cold 90% ethanol, dried in vacuo and dissolved in 100 μl of the TE solution.

(2) To 500 μl of the plasmid vector pUC119 (40 μg/ml) was added 160 units of BamHl (Toyobo), and the digestion reaction was allowed to proceed at 37° C. for 4 hours. After 2 phenol extractions, DNA was recovered by ethanol precipitation and dried in vacuo. Sterile water (400 μl), 50 μl of 0.5M Tris-HCl, pH 8.0 and 50 μl of alkaline phosphatase (Boehringer) (1 unit/μl) were added to the DNA and, after mixing, followed by 3 phenol extractions and ethanol precipitation. The DNA thus recovered was dissolved in 50 μl of the TE solution.

(3) To 10 μl of the DNA-containing TE solution obtained as described above in (1) were added 10 μl of the DNA-containing TE solution obtained as described above in (2), 7 μl of T4 ligase (Toyobo) (5 units/μl) and 3 μl of a buffer solution (660 mM Tris-HCl, pH 7.6, 66 mM MgCl₂, 100 mM dithiothreitol, 660 μM ATP). After mixing, the ligation reaction was conducted at 16° C. for 16 hours.

EXAMPLE 3

Identification of an IAA synthetase-encoding clone (1) The ligation reaction mixture obtained as described in Example 2-(3) was added to competent DH5α cells prepared by the method of Hanahan (J. Mol. Biol., 166, 557, 1983) for transformation of said cells. The cells were sown onto L agar medium containing 100 ppm of ampicillin and 40 ppm of Xgal and cultured at 37° C. for 24 hours. White colonies that had appeared were picked up and respectively cultured in a liquid LB medium containing 100 ppm of ampicillin and a strain producing IAA in said medium was selected as a clone holding an IAA synthetase gene. The ability to produce IAA was checked by growing each transformant in the conventional manner and judging, by high-performance liquid chromatography, whether IAA was produced in the culture.

(2) The above-mentioned IAA-producing strain was suspension-cultured in L medium. Cells were collected and the plasmid DNA was extracted therefrom by the alkaline minipreparation method (Nuclear Acids Res., 7 (6), 1513–1523, 1979). This DNA was cleaved with BamHI and subjected to 0.8% agarose gel electrophoresis, which confirmed the insertion of a foreign DNA of about 4 kbp. A pUC119 transformant carrying this insert of about 4 kbp was named pIA119.

EXAMPLE 4

Sequencing of the IAA synthetase gene (1) The *Escherichia coli* strain DH5α transformed with the plasmid pIA119 by a conventional method was cultured in 100 ml of LB medium overnight at 37° C. and cells were collected by centrifuging the culture at 10,000 revolutions per minute for 20 minutes. To the cells were added 200 ml of a TES solution (0.1M Tris-HCl, 0.02M EDTA, 25% sucrose, pH 8.0), 0.4 ml of RNase A (5 mg/ml) and 0.4 ml of egg white lysozyme (30 mg/ml) to give a cell suspension, which was maintained at 37° C. for 2 hours to allow the reaction to proceed. Then 8 ml of 20% SDS solution was added and the resultant mixture was stirred gently at room temperature. After the mixture became clear and transparent, 1.6 ml of 3 N NaOH was added and the resultant mixture was shaken gently at room temperature for 1 hour. Thereto was added 6 ml of 2M Tris-HCl (pH 7.0), followed by 2 minutes of gentle stirring. Thereafter, 10 ml of 5M NaCl was added and the mixture was stirred again gently and then allowed to stand overnight at 0° C. The mixture was then centrifuged at 5° C. and 10,000 revolutions per minute for 15 minutes. The supernatant was separated and one-tenth volume of polyethylene glycol #1000 (Nakalai Tesque) was added thereto. The mixture was stirred gently and then allowed to stand overnight at 0° C. The resultant precipitate was recovered by centrifugation (10,000 revolutions per minute, 15 minutes, 5° C.) and dissolved in 3.5 ml of the TESH solution by adding the solution thereto. To the resultant solution was added 4.4 g of CsCl (Nakalai Tesque) and 0.5 ml of an ethidium bromide solution (5 mg/ml). After mixing, the resultant mixture was centrifuged at 3,500 revolutions per minute for 10 minutes to eliminate the precipitate occurring on the surface of the aqueous layer. The solution obtained was centrifuged at 50,000 revolutions per minute at 20° C. for 16 hours and the second (from the top) band so identified under ultraviolet irradiation was recovered as plasmid DNA. This solution was subjected to 4 repetitions of butanol extraction for elimination of the ethidium bromide and then dialyzed against the TE solution for purification of the plasmid pIA119.

(2) Both ends of the insert DNA in the purified plasmid pIA119 were deleted using the EXO/MUNG system (Stratagene) and *Escherichia coli* DH5α transformants carrying the respective deletion product DNAs were checked as to whether they had IAA producing activity. As a result, it was found that a DNA of 1.65 kbp is the minimum DNA fragment necessary for the production of IAA. Then, the 1.65 kbp DNA was curtailed from the 5' terminus using the EXO/MUNG system to give 10 deletion product DNAs differing in length by about 200 bp. Furthermore, the 1.65 kbp insert DNA was subcloned into the plasmid pUC118 (Takara Shuzo) between the sites for recognition by EcoRI and HindIII (Toyobo) and curtailed in the same manner from the 5' terminus, whereby 10 deletion products DNAs resulting from reverse direction curtailment were obtained.

(3) The 20 deletion product DNAs obtained as mentioned above were introduced into *Escherichia coli* JM109 by a conventional method. Single-stranded DNAs were recovered therefrom by the method of Messing (Vieira, J. and Messing, J., Methods in Enzymology, 153, 3–11 (1987)) and the base sequence of the 1.65 kbp insert DNA was determined by the dideoxy method of Sanger et al. The base sequence of the IAA biosynthesis gene as revealed by analyzing the base sequence of the 1.65 kbp insert DNA and the corresponding amino acid sequence are shown in FIGS. 1A–1C.

While the invention has been described in detail and with reference to specific embodiments thereof, it will be apparent to one skilled in the art that various changes and modifications can be made therein without departing from the spirit and scope thereof.

What is claimed is:

1. A nucleic acid comprising an isolated structural gene of *Enterobacter cloacae* which encodes an enzyme with an amino acid sequence illustrated as SEQ ID NO. 2 involved in the biosynthesis of indoleacetic acid from tryptophan via indolepyruvic acid and indoleacetaldehyde as intermediates.

2. A nucleic acid according to claim 5, which has a base sequence illustrated as SEQ ID NO. 1.

3. A nucleic acid according to claim 1, wherein said *Enterobacter cloacae* is FERM BP-1529.

* * * * *